United States Patent
Choi et al.

(10) Patent No.: US 9,751,819 B2
(45) Date of Patent: Sep. 5, 2017

(54) METHOD OF PREPARING BUTADIENE

(71) Applicant: LG CHEM, LTD., Seoul (KR)

(72) Inventors: Dae Heung Choi, Daejeon (KR); Dong Hyun Ko, Daejeon (KR); Myung Ji Suh, Daejeon (KR); Kyong Yong Cha, Daejeon (KR); Ye Seul Hwang, Daejeon (KR); Jun Han Kang, Daejeon (KR); Hyun Seok Nam, Daejeon (KR); Joo Hyuck Lee, Daejeon (KR); Sang Jin Han, Daejeon (KR); Jun Kyu Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/035,430

(22) PCT Filed: Nov. 25, 2015

(86) PCT No.: PCT/KR2015/012694
§ 371 (c)(1),
(2) Date: May 9, 2016

(87) PCT Pub. No.: WO2016/099046
PCT Pub. Date: Jun. 23, 2016

(65) Prior Publication Data
US 2016/0347685 A1 Dec. 1, 2016

(30) Foreign Application Priority Data

Dec. 16, 2014 (KR) .................. 10-2014-0181338
Nov. 24, 2015 (KR) .................. 10-2015-0164750

(51) Int. Cl.
*C07C 5/327* (2006.01)
*C07C 5/333* (2006.01)
*C07C 5/48* (2006.01)
*B01J 23/00* (2006.01)
*B01J 23/887* (2006.01)

(52) U.S. Cl.
CPC ............... *C07C 5/48* (2013.01); *B01J 23/00* (2013.01); *B01J 23/002* (2013.01); *B01J 23/8876* (2013.01); *B01J 2523/00* (2013.01); *C07C 2523/02* (2013.01); *C07C 2523/887* (2013.01)

(58) Field of Classification Search
CPC .............................. C07C 5/327; C07C 5/333
USPC .................. 585/616, 621, 624, 625, 626
See application file for complete search history.

(56) References Cited

U.S. PATENT DOCUMENTS

| | | | |
|---|---|---|---|
| 2011/0004041 A1 | 1/2011 | Chung et al. | |
| 2012/0130137 A1 | 5/2012 | Orita et al. | |
| 2013/0281748 A1 | 10/2013 | Cha et al. | |

FOREIGN PATENT DOCUMENTS

| | | |
|---|---|---|
| CN | 103298771 A | 9/2013 |
| JP | S49-003498 B2 | 1/1974 |
| JP | S49-030805 | 8/1974 |
| JP | S49-101304 | 9/1974 |
| JP | S50-011886 | 5/1975 |
| JP | 2011-006395 A | 1/2011 |
| KR | 10-2011-0106181 A | 9/2011 |
| KR | 10-2011-0130130 A | 12/2011 |
| KR | 1020130036470 A | 4/2013 |
| KR | 10-2014-0131870 A | 11/2014 |
| WO | 2013161703 A1 | 10/2013 |
| WO | 2014182026 A1 | 11/2014 |

OTHER PUBLICATIONS

Yang et al., "Effect of steam on the oxidative dehydrogenation of butene over magnesium ferrites with and without chromium substitution," Applied Catalysis 70: 161-173 (1991).

*Primary Examiner* — Thuan D Dang
(74) *Attorney, Agent, or Firm* — Dentons US LLP

(57) ABSTRACT

The present invention relates to a method of preparing butadiene. More particularly, the present invention relates to a method of preparing butadiene by feeding butene and oxygen into a reactor containing a composite metal oxide catalyst and performing oxidative dehydrogenation, wherein a mole ratio of the oxygen to the butene is 1.8 to 2.2.

In accordance with the present invention, a method of preparing butadiene to secure long-term operation stability by maintaining the intensity of a catalyst despite oxidative dehydrogenation and not to decrease selectivity due to less side reaction is provided.

9 Claims, No Drawings

METHOD OF PREPARING BUTADIENE

CROSS-REFERENCE TO RELATED APPLICATION(S)

This application is a National Stage Entry of International Application No. PCT/KR2015/012694, filed Nov. 25, 2015, and claims the benefit of Korean Application No. 10-2014-0181338, filed on Dec. 16, 2014, and 10-2015-0164750, filed Nov. 24, 2015, all of which are hereby incorporated by reference in their entirety for all purposes as if fully set forth herein.

TECHNICAL FIELD

The present invention relates to a method of preparing butadiene. More particularly, the present invention relates to a method of preparing butadiene to secure long-term operation stability by maintaining the intensity of a catalyst despite oxidative dehydrogenation and not to decrease selectivity due to less side reaction.

BACKGROUND ART

Demand for 1,3-butadiene, as a petrochemical intermediate, and value thereof are gradually increasing.

As methods of preparing 1,3-butadiene, there are naphtha cracking, direct dehydrogenation of butene, oxidative dehydrogenation of butene, etc.

Thereamong, oxidative dehydrogenation of butene, as a reaction generating 1,3-butadiene and water by reaction of butene with oxygen, generates stable water, thus being very thermodynamically advantageous.

In addition, since the oxidative dehydrogenation of butene is an exothermic reaction unlike the direct dehydrogenation of butene, it enables production of 1,3-butadiene in a high yield even at low reaction temperature, compared to direct dehydrogenation. In addition, in the case of the oxidative dehydrogenation, additional heat supply is not necessary, thereby being very suitable for a commercialization process.

However, after the oxidative dehydrogenation of butene, the intensity of a catalyst is decreased, thereby elevating differential pressure of a reactor.

RELATED ART DOCUMENT

Patent Document

Japanese Patent Laid-Open Publication No. 2011-006395 (published on 13 Jan. 2011).

DISCLOSURE

Technical Problem

Therefore, the present invention has been made in view of the above problems, and it is one object of the present invention to provide a method of preparing butadiene to secure long-term operation stability by maintaining the intensity of a catalyst despite oxidative dehydrogenation and not to decrease selectivity due to less side reaction.

The above and other objects can be accomplished by the present invention described below.

Technical Solution

In accordance with one aspect of the present invention, provided is a method of preparing butadiene by feeding butene and oxygen into a reactor containing a composite metal oxide catalyst and performing oxidative dehydrogenation, wherein a mole ratio of the oxygen to the butene is 1.8 to 2.2.

Advantageous Effects

As apparent from the fore-going, the present invention advantageously provides a method of preparing butadiene to secure long-term operation stability by maintaining the intensity of a catalyst and inhibiting differential pressure elevation of a reactor despite oxidative dehydrogenation and not to decrease selectivity due to less side reaction.

BEST MODE

Now, the present invention will be described in more detail.

The present inventors confirmed that, when butene and oxygen ($O_2$) are fed in a predetermined ratio into a reactor, the intensity of a catalyst filled in the reactor is maintained, whereby long-term operation stability is secured and butadiene selectivity is not decreased. Based on this, the present invention was completed.

A method of preparing butadiene according to the present invention is characterized in that butadiene is prepared by feeding butene and oxygen into a reactor containing a composite metal oxide catalyst and performing oxidative dehydrogenation, wherein a mole ratio of the oxygen to the butene is 1.8 to 2.2. When the mole ratio of the oxygen to the butene is less than 1.8, lattice oxygen in the catalyst is consumed and thus structural stability is destroyed, whereby the catalyst intensity is decreased. On the other hand, when the mole ratio of the oxygen to the butene is greater than 2.2, lots of by-products are generated and thus butadiene selectivity is decreased.

The butene may be, for example, 1-butene.

The purity of the butene may be, for example, 95% or more, 98% or more, or 99% or more.

In the oxidative dehydrogenation, a gas hourly space velocity (GHSV) based on butene may be, for example, 30 to 80 $h^{-1}$BE (butene), 40 to 200 $h^{-1}$BE, or 50 to 150 $h^{-1}$BE. Within this range, a high conversion rate and high selectivity are exhibited.

In the reaction, for example, at least one selected from the group consisting of steam, carbon dioxide, and nitrogen may be further included.

When all of butene, oxygen, steam, and nitrogen are included in the reaction, a mole ratio thereof, i.e., a mole ratio of butene:oxygen:steam:nitrogen, may be, for example, 1:1.8 to 2.2:1 to 12:10 to 30, 1:1.8 to 2.2:1 to 10:10 to 25, or 1:1.8 to 2.2:1 to 8:12 to 25. Within this range, superior operation stability and selectivity are provided.

The oxidative dehydrogenation may be carried out, for example, at a reaction temperature of 250 to 450° C., 290 to 400° C., or 290 to 350° C.

When carbon dioxide, as an example, is additionally added to the reaction, a step of recycling carbon dioxide after the reaction may be further included.

The composite metal oxide catalyst may be, for example, a compound represented by Formula 1 below. In this case, superior butene conversion ratio and butadiene selectivity are provided.

$$Mo_aBi_bFe_cCo_dE_eO_y \qquad \text{[Formula 1]}$$

wherein E is at least one selected from the group consisting of nickel, sodium, potassium, rubidium, and cesium;

when a is 12, each of b, c, d, and e is 0.1 to 10, 0.1 to 10, 1 to 20, 0 to 5; y is a value determined to adjust valence to other ingredients.

E may be, for example, cesium, potassium or a mixture thereof. In this case, superior butene conversion ratio and butadiene selectivity are provided.

When E is cesium and potassium, a mole ratio of molybdenum:bismuth:iron:cobalt:cesium:potassium in Formula 1 may be, for example, 12:0.1 to 10:0.1 to 10:1 to 20:0 to 5:0 to 3. In another embodiment, the mole ratio may be 12:0.5 to 2:0.5 to 2:5 to 15:0 to 1:0 to 0.5, particularly 12:0.8 to 2:0.8 to 2:6 to 10:0 to 0.9:0 to 0.5, or 12:0.8 to 2:0.8 to 2:6 to 10:0.01 to 0.9:0.01 to 0.5. Within this range, a conversion ratio, selectivity and yield of a product are excellent.

The intensity of the composite metal oxide catalyst may be, for example, 3.0 or more kgf/cm$^2$, 3.0 to 6.0 kgf/cm$^2$, or 3.0 to 5.0 kgf/cm$^2$. Within this range, superior long-term operation stability and butadiene selectivity are provided.

The bismuth molybdate-based composite oxide catalyst may be prepared according to, for example, the following preparation step:

1) a step of preparing a first solution including at least one metal precursor among a bismuth precursor; an iron precursor; a cobalt precursor; and nickel, sodium, potassium, rubidium and cesium; 2) a step of adding the first solution to a second solution containing a molybdenum precursor dissolved therein and mixing and reacting the same; and 3) drying, molding, and firing after the reaction.

Each of the metal precursors used in step 1) is not specifically limited and may be any one used in the art.

In a specific example, although the nickel, sodium, potassium, rubidium and cesium precursors are not specifically limited, they may be an ammonium, a carbonate, a nitrate, an acetate, an oxide, or the like of the each metal. In another example, the bismuth precursor may be bismuth nitrate and the molybdenum precursor may be ammonium molybdate.

Step 1) is a step of preparing a first solution by adding each of the metal precursors to a solvent and mixing the same so as to mix metal ingredients constituting a bismuth molybdate-based composite oxide. The solvent may be distilled water, but the present invention is not limited thereto. Here, so as to increase solubility of the bismuth precursor, a strong acid may be additionally added to the solvent. Alternatively, the bismuth precursor may be added to a solution including the different metal precursor after being dissociated and dissolved in the solvent including a strong acid to prepare a first solution. The strong acid may be nitric acid, but the present invention is not limited thereto.

Step 2) is a step of preparing a second solution by dissolving the molybdenum precursor in a solvent and then adding the first solution thereto and mixing to mix the first solution with the molybdenum precursor. Here, the reaction may be carried out while stirring. The stirring may be carried out at 25 to 80° C., 100 to 800 rpm.

Step 3) is a step of obtaining a bismuth molybdate-based composite oxide by drying, molding and firing a reaction product generated after the reaction. The firing may be carried out, for example, 400 to 600° C. for 1 to 24 hours, preferably at 450 to 500° C. for 2 to 10 hours.

A reactor used in the oxidative dehydrogenation is not specifically limited so long as the reactor is generally used in the art. For example, the reactor may be a tubular reactor, a tank reactor, a fluidized bed reactor, or a fixed bed reactor.

The fixed bed reactor may be, for example, a multitubular reactor or a plate type reactor.

The reactor may be, for example, a reactor, in which reaction temperature of a catalyst layer is constantly maintained and oxidative dehydrogenation is preceded while a reaction product continuously passes through the catalyst layer, installed in a reactor.

Hereinafter, the present invention will be described in detail with reference to exemplary embodiments thereof for the purposes of promoting an understanding of the principles of the invention. These exemplary embodiments are provided for illustrative purposes only and should not be construed as limiting the scope and spirit of the present invention and are obvious to those of ordinary skill in the art to which the present invention pertains. In addition, those of ordinary skill in the art may carry out a variety of applications and modifications based on the foregoing teachings within the scope of the present invention, and these modified embodiments may also be within the appended claims of the present invention.

EXAMPLES

Preparation Example: Preparation of Bismuth Molybdate-Based Composite Oxide Catalyst Bismuth nitrate pentahydrate $(Bi(NO_3)_{3.5}(H_2O))$, iron nitrate nonahydrate $(Fe(NO_3)_3.9(H_2O))$, cobalt nitrate hexahydrate $(Co(NO_3)_2.6(H_2O))$, potassium nitrate $(KNO_3)$, and cesium nitrate $(CsNO_3)$ are dissolved in distilled water to prepare a first solution. Here, the bismuth nitrate pentahydrate was added to the distilled water after being separately dissolved in an aqueous nitric acid solution.

In addition, ammonium molybdate tetrahydrate $((NH_4)_6(Mo_7O_{24}).4(H_2O))$ was dissolved in distilled water to prepare a second solution.

The first solution was added to the second solution and then stirred at 40° C. for one hour, thereby generating a precipitate. The generated precipitate was dried in a 120° C. oven for 24 hours and then fired at 450° C. for five hours, thereby preparing $Mo_{12}Bi_{0.8\ to\ 2}Fe_{0.8\ to\ 2}Co_{6\ to\ 10}Cs_{0.01\ to\ 0.9}K_{0.01\ to\ 0.5}O_y$, where y is a mole number of an oxygen element satisfying valences with other constituting elements except for oxygen, as a multi-component bismuth molybdate catalyst.

Example 1 and Comparative Examples 1 to 6

1-butene and oxygen were used as reactants, and nitrogen and steam were additionally added thereto. A tubular metal reactor was used as a reactor. A reaction device was designed as follows: a previously prepared composite metal oxide catalyst was filled in the reactor such that the volume of a catalyst layer which the reactants contacted was fixed to 50 cc; and water was introduced by means of a vaporizer and vaporized at 340° C. as steam such that the steam was mixed with 1-butene and oxygen as other reactants and introduced into the reactor. The amount of butene was controlled by means of a mass flow controller for liquid, and oxygen and nitrogen were controlled by means of a mass flow controller for gas. The introduction rate of steam was controlled by means of a liquid pump. In addition, proportions and gas hourly space velocities (GHSV) among the reactants were set based on water and 1-butene.

Under a condition of GHSV and OBR (mole ratio of oxygen to butene $(O_2/C_4H_8)$) summarized in Table 1 below and using butene and nitrogen in a mole ratio of 1:12, a reaction was carried out during an operation time summarized in Table below while maintaining reaction temperature at 320° C. After the reaction, a product was analyzed though gas chromatography.

Test Examples

Reaction characteristics of composite metal oxide catalysts used in Example 1 and Comparative Examples 1 to 6 were measured according to the following methods. Results are summarized in Table 1 below.

Catalyst intensity (kgf): Measured in a horizontal direction by means of a tensile strength measurer.

Oxygen reduction rate in catalyst (%): Measured by means of energy-dispersive X-ray spectroscopy (EDX).

Catalyst intensity reduction rate (%): Calculated according to Equation 1 below:

Catalyst intensity reduction rate (%)=((catalyst intensity before reaction−catalyst intensity after reaction)/catalyst intensity before reaction)×100     [Equation 1]

Selectivity: Data obtained through gas chromatography was calculated according to Equation 2 below:

Selectivity (%)=(mole number of generated 1,3-butadiene/mole number of reacted 1-butene)×100     [Equation 2]

TABLE 1

| | OBR | GHSV (h−1 BE) | Operation time | Oxygen content change ratio in catalyst | Catalyst intensity reduction rate | Intensity Before reaction | Intensity After reaction |
|---|---|---|---|---|---|---|---|
| Example 1 | 1.8 | 38 | 40 hr | <0.1% | <0.1% | 3.18 | 3.22 |
| Comparative Example 1 | 1.5 | 38 | 40 hr | 19% reduction | 32.7% | 3.18 | 2.14 |
| Comparative Example 2 | 1.0 | 75 | 39 days | 19% reduction | 11.3% | 3.28 | 2.91 |
| Comparative Example 3 | 1.0 | 75 | 37 days | 11% reduction | 18.6% | 3.18 | 2.59 |

TABLE 2

| | OBR | GHSV (h−1 BE) | Operation time | Conversion ratio (%) | Selectivity (%) | Yield (%) |
|---|---|---|---|---|---|---|
| Example 1 | 1.8 | 38 | 40 hr | 98.15 | 90.45 | 88.78 |
| Comparative Example 4 | 2.3 | 38 | 40 hr | 98.53 | 86.09 | 84.82 |

As shown in Table 1, it can be confirmed that, in the method of preparing butadiene (Example 1) according to the present invention, oxygen content reduction in the catalyst and catalyst intensity reduction are not almost observed and, when OBR is less than 1.8 as in conventional technology or Comparative Examples 1 to 3, lattice oxygen in the catalyst during the reaction is escaped and thus the intensity of the catalyst is decreased.

In addition, it can be confirmed that, as in Comparative Example 4, butadiene selectivity is greatly decreased when OBR is greater than 2.2.

The invention claimed is:

1. A method of preparing butadiene, comprising:
feeding 1-butene, oxygen, nitrogen and steam into a reactor containing a composite metal oxide catalyst, wherein:
a mole ratio of the butene to the nitrogen is 1:10 to 30; and
the composite metal oxide catalyst comprises a composite metal oxide of Formula 1:

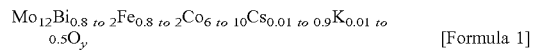

$$Mo_{12}Bi_{0.8\ to\ 2}Fe_{0.8\ to\ 2}Co_{6\ to\ 10}Cs_{0.01\ to\ 0.9}K_{0.01\ to\ 0.5}O_y \quad \text{[Formula 1]}$$

wherein y is a value determined to adjust valence to other constituting elements; and performing oxidative dehydrogenation of the 1-butene to produce butadiene, wherein a mole ratio of the oxygen to the butene is 1.8 to 2.2.

2. The method according to claim 1, wherein the butene is 1-butene.

3. The method according to claim 1, wherein, in the oxidative dehydrogenation, a gas hourly space velocity (GHSV) based on butene is 30 to 80 h$^{-1}$.

4. The method according to claim 1, wherein, in the oxidative dehydrogenation, carbon dioxide is further included.

5. The method according to claim 1, wherein, in the reaction, a mole ratio of butene:steam is 1:1 to 12.

6. The method according to claim 1, wherein the reactor is a tubular reactor, a tank reactor, a fluidized bed reactor, or a fixed bed reactor.

7. The method according to claim 1, wherein the oxidative dehydrogenation is carried out at a temperature of 320° C.

8. The method according to claim 1, wherein the steam is introduced into the reactor using a vaporizer and vaporized at a temperature of 340° C.

9. The method according to claim 1, wherein a mole ratio of the oxygen to the butene is 1.8.

* * * * *